(12) United States Patent
Tsukagoshi et al.

(10) Patent No.: US 9,282,935 B2
(45) Date of Patent: Mar. 15, 2016

(54) X-RAY CT APPARATUS

(71) Applicants: Kabushiki Kaisha Toshiba, Tokyo (JP); Toshiba Medical Systems Corporation, Otawara-shi (JP)

(72) Inventors: Shinsuke Tsukagoshi, Nasushiobara (JP); Tatsuro Suzuki, Utsunomiya (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 135 days.

(21) Appl. No.: 14/007,847

(22) PCT Filed: Feb. 14, 2013

(86) PCT No.: PCT/JP2013/053574
§ 371 (c)(1),
(2) Date: Sep. 26, 2013

(87) PCT Pub. No.: WO2013/125448
PCT Pub. Date: Aug. 29, 2013

(65) Prior Publication Data
US 2014/0037047 A1    Feb. 6, 2014

(30) Foreign Application Priority Data

Feb. 24, 2012 (JP) ................................. 2012-038385
Feb. 13, 2013 (JP) ................................. 2013-025411

(51) Int. Cl.
*A61B 6/03* (2006.01)
*A61B 6/06* (2006.01)
*A61B 6/00* (2006.01)

(52) U.S. Cl.
CPC . *A61B 6/032* (2013.01); *A61B 6/06* (2013.01); *A61B 6/4266* (2013.01)

(58) Field of Classification Search
CPC .......... A61B 6/03; A61B 6/42; A61B 6/4208; A61B 6/4266
USPC ............................................. 378/4, 15, 16, 19
See application file for complete search history.

(56) References Cited

U.S. PATENT DOCUMENTS 7,453,978 B1 * 11/2008 DiBianca et al. ............... 378/19
2002/0080910 A1 * 6/2002 Kuroda ........................... 378/19

(Continued)

FOREIGN PATENT DOCUMENTS

| CN | 1721876 A | 1/2006 |
|---|---|---|
| JP | 2001 54515 | 2/2001 |
| JP | 2006 15050 | 1/2006 |
| JP | 2009 28065 | 2/2009 |

(Continued)

OTHER PUBLICATIONS

Office Action and Search Report issued on Aug. 28, 2014 in the corresponding Chinese Patent Application No. 201380001325.5.

(Continued)

*Primary Examiner* — Jack Berman
*Assistant Examiner* — David E Smith
(74) *Attorney, Agent, or Firm* — Oblon, McClelland, Maier & Neustadt, L.L.P.

(57) ABSTRACT

An X-ray CT apparatus includes an X-ray tube, an X-ray detector, and a control unit. The X-ray detector includes at least two divided ranges. One range includes a small detection range in which X-ray detection elements of a small size for detecting the X-rays radiated from the X-ray tube are arrayed. The other range includes a large detection range in which the X-ray detection elements of a large size for detecting the X-rays radiated from the X-ray tube are arrayed. The control unit is configured to select the small detection range or the large detection range. The X-ray CT apparatus can efficiently achieve high resolution upon imaging and, further, is capable of fully utilizing X-ray detection elements of a small detector size.

17 Claims, 14 Drawing Sheets

(56) References Cited

U.S. PATENT DOCUMENTS

| | | | |
|---|---|---|---|
| 2006/0002508 A1* | 1/2006 | Yahata | 378/19 |
| 2006/0159222 A1* | 7/2006 | Altman | 378/15 |
| 2009/0028289 A1 | 1/2009 | Tsuyuki et al. | |
| 2011/0222646 A1* | 9/2011 | Suzuki et al. | 378/4 |
| 2011/0274237 A1* | 11/2011 | Muenker et al. | 378/4 |

FOREIGN PATENT DOCUMENTS

JP       2011 206534       10/2011

OTHER PUBLICATIONS

International Search Report Issued Mar. 12, 2013 in PCT/JP13/53574 filed Feb. 14, 2013.

* cited by examiner

X-RAY CT APPARATUS

FIELD OF THE INVENTION

The embodiments of the present invention relate to an X-ray CT apparatus.

BACKGROUND ART

Some conventional X-ray CT (computed tomography) systems detect X-rays radiated from an X-ray tube to a subject and transmitted through the subject with an X-ray detector, acquire projection data, then reconstruct images from the acquired projection data (for example, Patent Document 1.)

The X-ray tube includes an anode provided with a radiation surface for radiating X-rays, as well as a cathode provided with a filament. X-rays with a cone angle enlarging from the radiation surface in the rostrocaudal direction of the subject are radiated to the subject. The size of an effective focal point, which is the apparent size when seeing the radiation surface from the side on which the X-rays are radiated, is sometimes referred to as a focal point size.

The focal point size differs depending on whether seeing the radiation surface from the anode side or the cathode side. The radiation surface is structured such that the focal point size is decreased on the anode side and increased from the anode toward the cathode.

The X-ray detector comprises X-ray detection elements two-dimensionally arrayed in the rostrocaudal direction and horizontally orthogonal thereto. The X-ray detector includes a uniform type, a hybrid type, and a non-uniform type depending on the array mode.

In the uniform type of X-ray detector, the X-ray detection elements are uniformly arrayed in the rostrocaudal direction of the subject. The size of the X-ray detection element in the rostrocaudal direction is sometimes referred to as a detector size.

In the hybrid type, the X-ray detection elements of a small detector size are arrayed in a plurality of rows in the center in the rostrocaudal direction of the X-ray detector, with the X-ray detection elements of a large detector size arrayed every specific number of rows in front and back of those of the small detector size.

In the non-uniform type, the X-ray detection elements from the small detector size to the large detector size are symmetrically arrayed in front and back.

High resolution cannot be acquired upon imaging by detecting the X-rays radiated from the focal point of the small focal point size and transmitted through the subject with the X-ray detection elements of the large detector size, making it impossible to fully utilize the X-ray detection elements of the small detector size. High and low states of resolution are relatively defined in the following description.

PRIOR ART DOCUMENT

Patent Document

[Patent Document 1] Japanese Unexamined Patent Application Publication No. 2009-28065

SUMMARY OF THE INVENTION

Problems to be Solved by the Invention

However, the uniform type of X-ray detector has been problematic in that it is not efficient to use the X-ray detection elements of the small detector size for all X-ray detection elements of the X-ray detector in order to achieve high resolution efficiently upon imaging.

In addition, the hybrid type X-ray detector has been problematic in that the X-ray detection elements of the small detector size arrayed in a plurality of rows in the center and the focal point of the small focal point size do not always correspond to each other, making it impossible to fully utilize the X-ray detection elements of the small detector size.

Further, the non-uniform type of X-ray detector has been problematic in that the X-ray detection elements of the small detector size cannot be fully utilized similar to the hybrid type.

The present embodiments are intended to provide an X-ray CT apparatus capable of efficiently achieving high resolution upon imaging and, further, capable of fully utilizing the X-ray detection elements of the small detector size.

Means of Solving the Problems

In order to solve the above-described problems, the X-ray CT apparatus according to the present embodiments rotates an X-ray tube and an X-ray detector around a subject mounted on a table top, radiates X-rays with a cone angle enlarging from the X-ray tube to the subject, and acquires images of the subject based on the X-rays transmitted through the subject and detected by the X-ray detector. The X-ray detector includes at least two divided ranges. One range includes a small detection range in which X-ray detection elements of a small size for detecting the X-rays radiated from the X-ray tube are arrayed. The other range includes a large detection range in which X-ray detection elements of a large size for detecting the X-rays radiated from the X-ray tube are arrayed. The X-ray CT apparatus comprises a control unit configured to select the small detection range or the large detection range.

MODES FOR CARRYING OUT THE INVENTION

Figure 1:
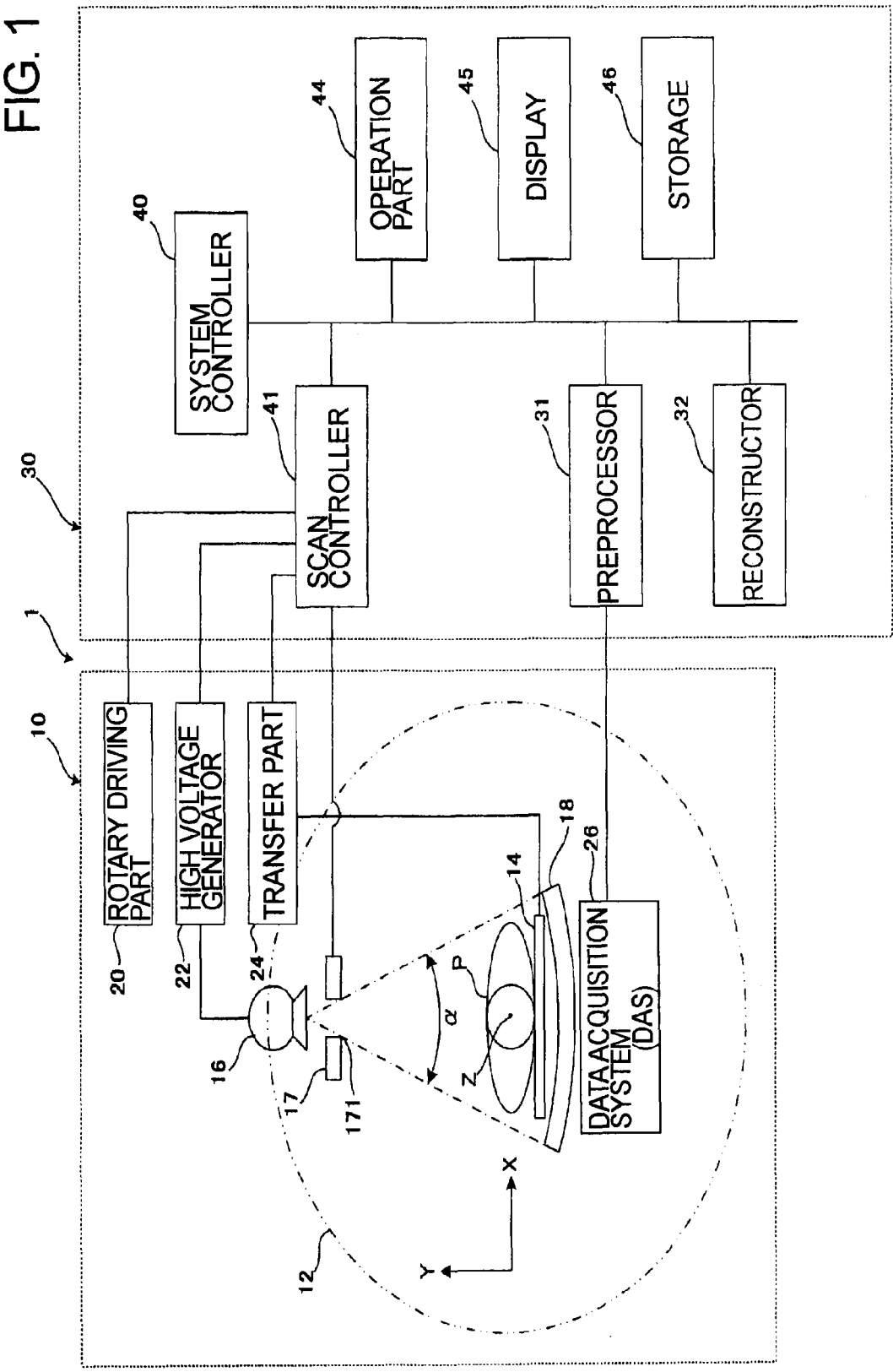
FIG. 1 is a block diagram illustrating a structure of an X-ray CT apparatus according to a first embodiment.

Hereinafter, various embodiments of the X-ray CT apparatus are described with reference to the drawings.
[First Embodiment]
A structure of an X-ray CT apparatus according to a first embodiment is described with reference to FIG. 1. FIG. 1 is a block diagram illustrating the structure of the X-ray CT apparatus.

As illustrated in FIG. 1, an X-ray CT apparatus 1 comprises a gantry 10 and a console 30.

The gantry 10 comprises a rotating frame 12, an X-ray tube 16, a collimator 17, an X-ray detector 18, a rotary driving unit 20, a high voltage generator 22, and a data acquisition system (DAS) 26.

The body of the gantry 10 rotatably supports the circular or discoid rotating frame 12. A scan region with a subject P mounted on a table top 14 to be inserted is formed on the inner circumference of the rotating frame 12.

A top transfer unit 24 is provided on a couch (not illustrated) so as to longitudinally transfer the table top 14 (in the rostrocaudal direction of the subject P). In addition, a lifting unit (illustration omitted) for vertically sliding the table top 14 is arranged on the couch.

An XYZ orthogonal coordinate system is defined here. A Z-axis is defined as a rotational axis of the rotating frame 12. The table top 14 is arranged such that a longitudinal direction thereof becomes parallel to the Z-axis direction. Accordingly, the body axis of the subject P becomes parallel to the Z-axis. An X-axis is defined as an axis in the horizontal direction, while the Y-axis is defined as an axis in the vertical direction.

The X-ray CT apparatus 1 has various types such as a ROTATE/ROTATE type in which the X-ray tube 16 is integrally rotated with the X-ray detector 18, and the like, around the subject, and a STATIONARY/ROTATE type in which many detection elements are arrayed in a ring-shape, with the X-ray tube 16 only rotated around the subject; however, any type thereof is applicable to the present embodiment. The X-ray CT apparatus 1 is described here as the ROTATE/ROTATE type.

The rotating frame 12 includes the X-ray tube 16, the collimator 17, and the X-ray detector 18.

The rotating frame 12 continuously rotates the X-ray tube 16 and the X-ray detector 18 while being supplied with driving signals from the rotary driving unit 20.

The X-ray tube 16 generates X-rays while being applied with a high voltage and supplied with a filament current from the high voltage generator 22.

The X-ray tube 16 and the X-ray detector 18 are arranged facing each other such that the subject P mounted on the table top 14 is sandwiched therebetween.

Figure 2:
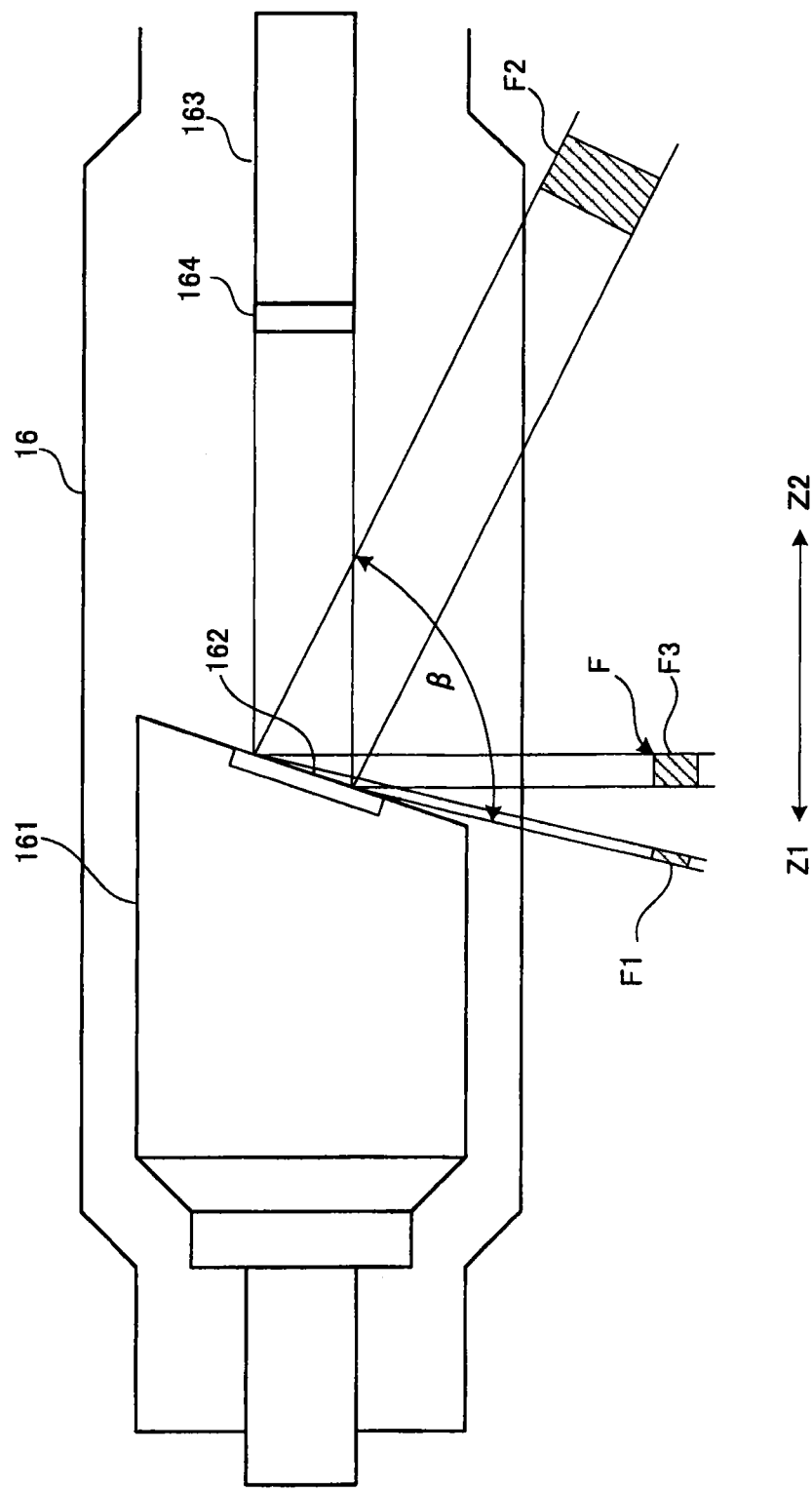
FIG. 2 is a conceptual illustration of an X-ray tube.

(X-ray Tube)
FIG. 2 is a conceptual illustration of the X-ray tube 16. As illustrated in FIG. 2, the X-ray tube 16 includes an anode 161 having a radiation surface (target) 162 for radiating X-rays and a cathode 163 having a filament 164. The X-rays with a cone angle (denoted by "β" in FIG. 2) enlarging from the radiation surface 162 in the rostrocaudal direction of the subject are radiated to the subject. The hatched focal point size (the size of the effective focal point F) illustrated in FIG. 2 differs depending on whether seeing the radiation surface near the anode 161 or the cathode 163. The cone angle enlarges in the rostrocaudal direction in the following description; however, this direction is obviously not limited to the rostrocaudal direction.

As illustrated in FIG. 2, the radiation surface as a plane with a specific angle with respect to the direction of the cathode 163 is structured such that the focal point size is decreased on the anode 161 side and increased from the anode 161 toward the cathode 163. FIG. 2 illustrates a focal point of a small focal point size, a focal point of a large focal point size, and a focal point of a middle focal point size which are respectively denoted as "F1," "F2," and "F3."

Figure 3:
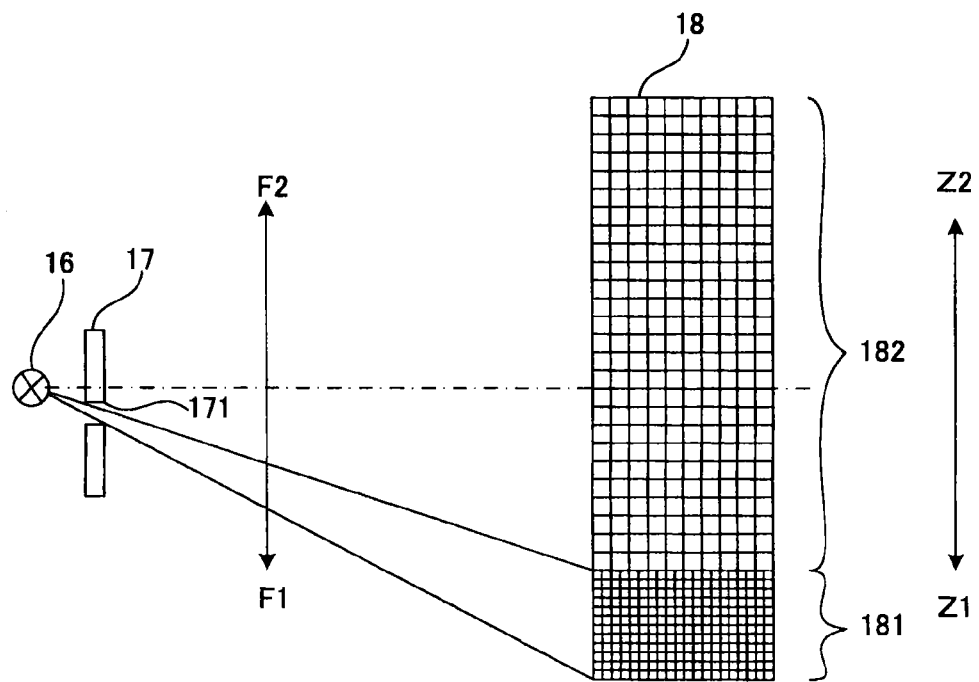
FIG. 3 is a drawing illustrating an X-ray detector including a small detection range at one end in a rostrocaudal direction.

Further, the anode 161 side on which the focal point size is decreased is sometimes referred to as an end side of the cone angle β or a Z1 (illustrated in FIG. 2) side. In addition, the cathode 163 side on which the focal point size is increased is sometimes referred to as the other end side of the cone angle β or a Z2 (illustrated in FIG. 2) side.
(Collimator)
As illustrated in FIG. 1, the collimator 17 with an aperture 171 through which the X-rays are transmitted is configured such that the path of the X-rays radiated to the subject is limited by adjusting the range and position of the aperture 171.
(X-ray Detector)
FIG. 3 is a drawing illustrating an X-ray detector 18 of a hybrid type including a small detection range 181 at one end in the rostrocaudal direction (Z direction). Here, the small detection range 181 means the range in which specific rows of the X-ray detection elements of the small detector size are arrayed. In addition, a large detection range 182 means the range in which specific rows of the X-ray detection elements of the large detector size are arrayed.

As illustrated in FIG. 3, the small detection range 181 is arranged at one end (Z1 side) of the X-ray detector 18, while the large detection range 182 is arranged in the center and at the other end (Z2 side) of the X-ray detector 18.

The X-ray detection elements (X-ray detection elements of a small detector size) with a detector size, that is a size in the rostrocaudal direction, of for example 0.5 mm, is used for the small detection range 181. The small detection range 181 is configured by arranging, in the Z-axis (body axis) direction, a specific number of rows of X-ray detection element groups including a plurality of X-ray detection elements arranged in the X-axis direction. When the X-ray detection elements are thus arranged in the Z-axis (body axis) direction, this arranging direction is sometimes referred to as the longitudinal direction.

The X-ray detection elements (X-ray detection elements of a large detector size) with a detector size of, for example 1.0 mm, are used for the large detection range 182. The large detection range 182 is configured by arranging, in the Z-axis (body axis) direction, many rows of X-ray detection element groups including a plurality of X-ray detection elements arranged in the X-axis direction.

An X-ray CT apparatus with a step and shoot technique for imaging by displacing the imaging regions of the subject radiates X-rays (cone beam) to the subject P every time the table top 14 is transferred in the rostrocaudal direction by a specific transfer amount.

The top transfer unit 24 transfers the table top 14 by a specific transfer amount under the control of a scan controller 41 in the console 30.

The radiation time interval of X-rays with respect to the subject is, for example, ten times per second. The high voltage generator 22 applies a high voltage and supplies a filament current to the X-ray tube 16 under the control of the scan controller 41 in the console 30.

The X-ray detector 18 detects the X-rays generated from the X-ray tube 16 and transmitted through the imaging region, and generates signals in accordance with the intensity of the detected X-rays. The data acquisition system (DAS) 26 is connected to the X-ray detector 18.

The data acquisition system 26 acquires current signals from the X-ray detector 18 under the control of the scan controller 41. The data acquisition system 26 generates projection data as a digital signal by amplifying the acquired current signals and digitally converting the amplified current signals. The projection data is supplied to the console 30 via a non-contact data transfer unit (illustration omitted) each time the projection data is generated. Projection data of a time series is generated by repeatedly performing CT scanning, and supplied to the console 30.

As illustrated in FIG. 1, the console 30 comprises a preprocessor 31, a reconstructor 32, a system controller 40, the scan controller 41, an operation unit 44, a display 45, and a storage 46. The system controller 40 and the scan controller 41 are sometimes referred to as the control unit.

The preprocessor 31 performs preprocessing such as a logarithmic transformation and sensitivity correction to the projection data supplied in real time from the data acquisition system 26. Projection data used for reconstructing images is generated by the preprocessing.

The reconstructor 32 generates CT image data in real time regarding the subject P based on the preprocessed projection data. In other words, the reconstructor 32 reconstructs CT image data (CT value) of a time series based on the projection data of the time series.

An image reconstruction method used by the X-ray CT apparatus includes a full-scan method and a half-scan method. The full-scan method requires the projection data for one circle around the subject, namely, about $2\pi$[rad] minutes, in order to reconstruct CT image data for one slice. In addition, the half-scan method requires the projection data for $\pi+\alpha$[rad] ($\alpha$: fan angle) minutes in order to reconstruct image data for one slice. Either of the full-scan method or the half-scan method is applicable to the present embodiment.

The system controller 40 functions as a central unit of the X-ray CT apparatus 1. Specifically, the system controller 40 reads out a control program stored in the storage 46 and develops the program in the memory, and controls each unit in accordance with the developed control program. Thereby, the system controller 40 can carry out CT scanning.

An example of the scan mode includes a first mode for limiting imaging to high resolution imaging, a second mode for limiting imaging to low resolution imaging, and a third mode for removing these limitations. Each of the first to third modes is allowed to correspond to the range and position of the aperture 171 of the collimator 17 and is stored, as a database, in the inner memory of the system controller 40 or the storage 46. The system controller 40 receives input regarding the first mode to the third mode, and outputs the range and position of the aperture 171 of the corresponding collimator 17 to the scan controller 41.

The scan controller 41 controls the gantry 10 (the collimator 17, the rotary driving unit 20, the high voltage generator 22, the top transfer unit 24, and the data acquisition system 26) in order to carry out CT scanning.

The scan controller 41 receives the range and position of the aperture 171 output from the system controller 40, thereby controlling the collimator 17.

When the system controller 40 receives the first mode, the scan controller 41 controls the collimator 17 to transfer the position of the aperture 171 by a specific amount from the initial position (center line: the dashed line illustrated in FIG. 3) in the Z1 direction and decrease the range of the aperture 171 from the initial value. Thereby, the small detection range (the X-ray detection element of the small detection size) 181 arranged on the Z1 side corresponds to a focal point F1 of the small focal point size on the Z1 side. Therefore, the X-ray detection elements of the small detector size can be fully utilized, further allowing high resolution to be efficiently achieved upon imaging.

In addition, the scan controller 41 outputs a specific transfer amount (for example, the amount corresponding to the width of the small detection range 181 in the Z direction) to the top transfer unit 24. The top transfer unit 24 transfers the table top 14 by each transfer amount. X-rays are radiated from the focal point F1 of the small focal point size to the subject transferred by each specific amount and detected by the small detection range 181, making it possible to image the subject at high resolution by detecting the X-rays.

A user sometimes wants to image the subject over a wide range even at low resolution, contrary to imaging at high resolution. Imaging the subject over a wide range at low resolution becomes possible by using the large detection range 182.

Figure 4:
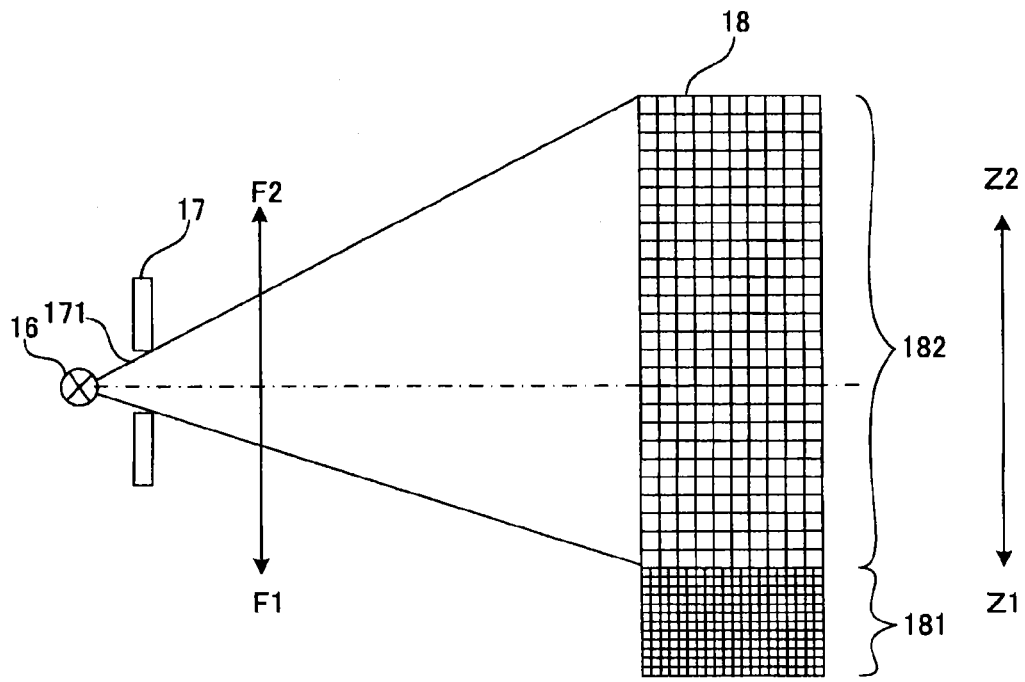
FIG. 4 is a drawing illustrating the X-ray detector when CT scanning is carried out in the second mode.

FIG. 4 is a drawing illustrating the X-ray detector 18 when CT scanning is carried out in the second mode. FIG. 4 illustrates the large detection range (the X-ray detection elements of the large detection size) 182 and the focal point F2 of a large focal point size, which correspond to each other. The large detection range 182 is wider than the small detection range 181 in terms of the size of the range in which X-rays are detected.

When the system controller 40 receives the second mode, the scan controller 41 controls the collimator 17 to transfer the position of the aperture 171 by a specific amount from the initial position (center line: the dashed line illustrated in FIG. 4) in the Z2 direction and decrease the range of the aperture 171 from the initial value. Thereby, the large detection range 182 arranged on the Z2 side corresponds to the focal point F2 of the large focal point size on the Z2 side.

In addition, the scan controller 41 outputs a specific transfer amount (for example, the amount corresponding to the width of the large detection range 182 in the Z direction) to the top transfer unit 24. The top transfer unit 24 transfers the table top 14 by each transfer amount. X-rays are radiated from the focal point F2 of the large focal point size to the subject transferred by each specific amount and detected by the large detection range 182, making it possible to image the subject at low resolution over a wide range.

The operation unit 44 receives various instructions and information input from the operator. For example, the operation unit 44 inputs a scan mode by the user through an input device. Available input devices include a key board, a mouse, a switch, and the like.

The display 45 displays CT images on a display device. Available display devices include, for example, a CRT display, a liquid crystal display, an organic EL display, a plasma display, and the like.

The storage 46 stores the projection data and the CT image data. Further, the storage 46 stores the control program in advance.

[Operations]

Figure 5:
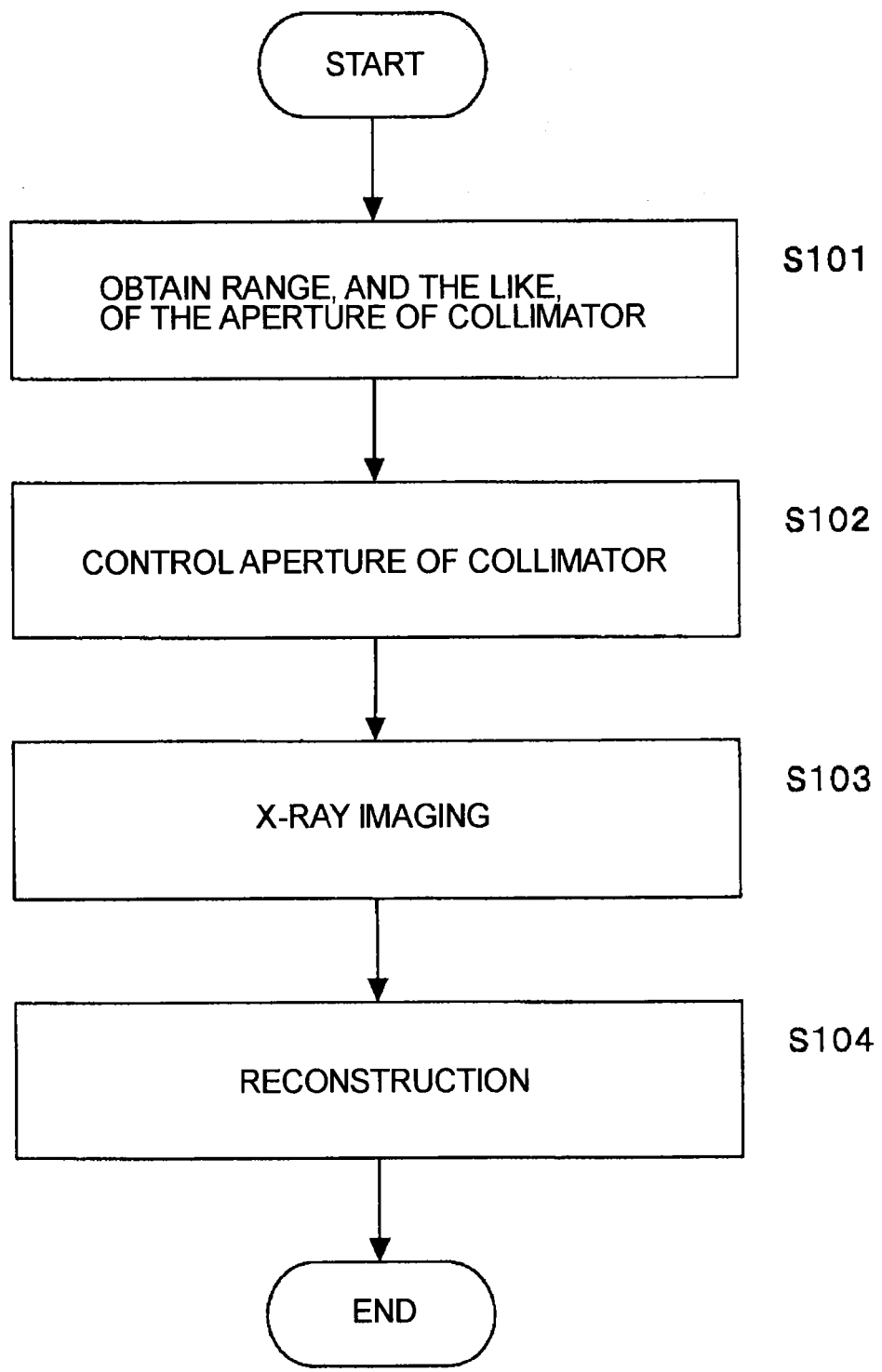
FIG. 5 is a flowchart illustrating operations of the X-ray CT apparatus.

Subsequently, CT scanning to be carried out by the X-ray CT apparatus 1 is described with reference to FIG. 5. FIG. 5 is a flowchart illustrating operations of the X-ray CT apparatus 1. Here, the description is provided assuming that the first mode is input in the system controller 40 by operating the operation unit 44.

(S101: Obtain Range, and the like, of the Aperture)

The system controller 40 obtains the range and position of the aperture 171 of the collimator 17 corresponding to the input first mode, and outputs the range, and the like of the obtained aperture 171 to the scan controller 41.

(S102: Control Aperture)

When entering the first mode in the system controller 40, the scan controller 41 controls the collimator 17 based on the range and position of the aperture 171 of the collimator 17 corresponding to the first mode. It becomes possible to allow the small detection range (the X-ray detection elements of the small detector size) 181 to correspond to the focal point F1 of the small focal point size by adjusting the range and position of the aperture 171.

(S103: X-ray Imaging)

The small detection range 181 detects the X-rays radiated from the focal point F1 of the small focal point size and transmitted through the subject. Thereby, high resolution can be achieved upon imaging.

(S104: Reconstruction)

DAS 26 acquires projection data from the X-rays detected by the small detection range 181. The reconstructor 32 reconstructs images based on the projection data, making it possible to obtain images at high resolution.

Figure 6:
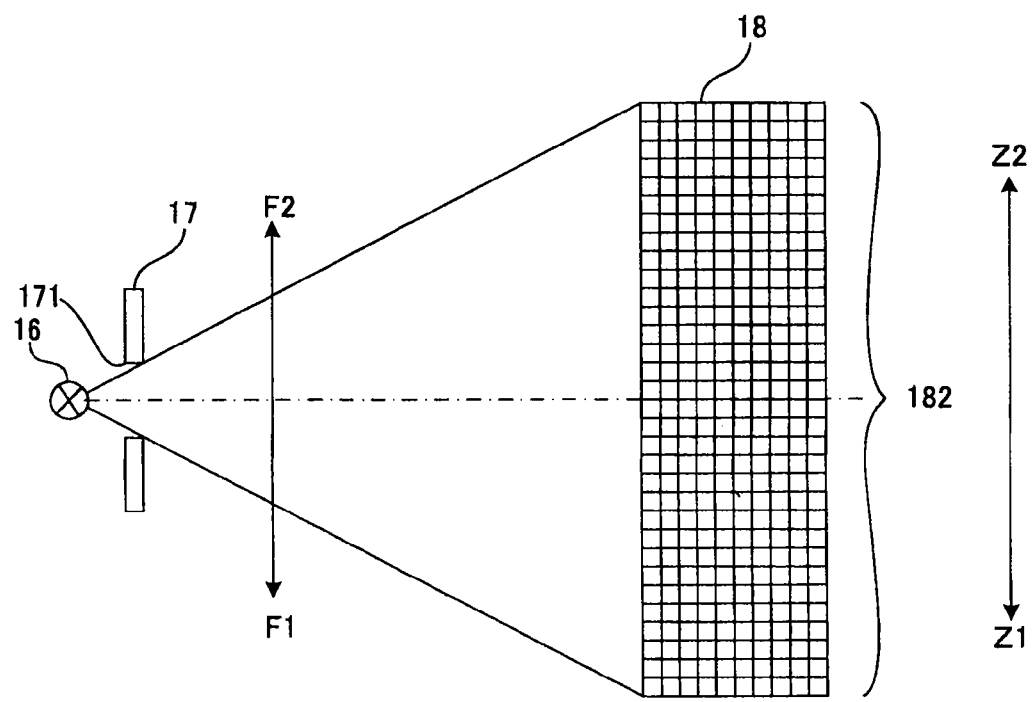
FIG. 6 is a drawing illustrating an X-ray detector of a uniform type according to a comparative example.

Here, the X-ray detector 18 illustrated in FIG. 3 is described with reference to a comparative example. FIG. 6 is a drawing illustrating the X-ray detector 18 of a uniform type according to the comparative example. As illustrated in FIG. 6, in the uniform type of X-ray detector 18, the X-ray detection elements of the large detector size of 1.0 mm are uniformly arrayed in the X-Z direction. In other words, the X-ray detector 18 is entirely configured by the large detection range 182.

The X-ray detector 18 illustrated in FIG. 6 is entirely configured by the large detection range 182 so that even if the range and position of the aperture 171 are adjusted, the large detection range 182 corresponds to the focal point F1 of the small focal point size. However, high resolution cannot be achieved upon imaging even if the large detection range 182 is allowed to correspond to the focal point F1 of the small focal point size.

On the other hand, it is inefficient to use a small detector size for all X-ray detection elements of the X-ray detector illustrated in FIG. 6.

On the contrary, in the X-ray detector 18 illustrated in FIG. 3, high resolution can be achieved upon imaging by providing the small detection range 181 on one end of the X-ray detector 18, and allowing this small detection range 181 to correspond to the focal point F1 of the small focal point size.

Figure 7:
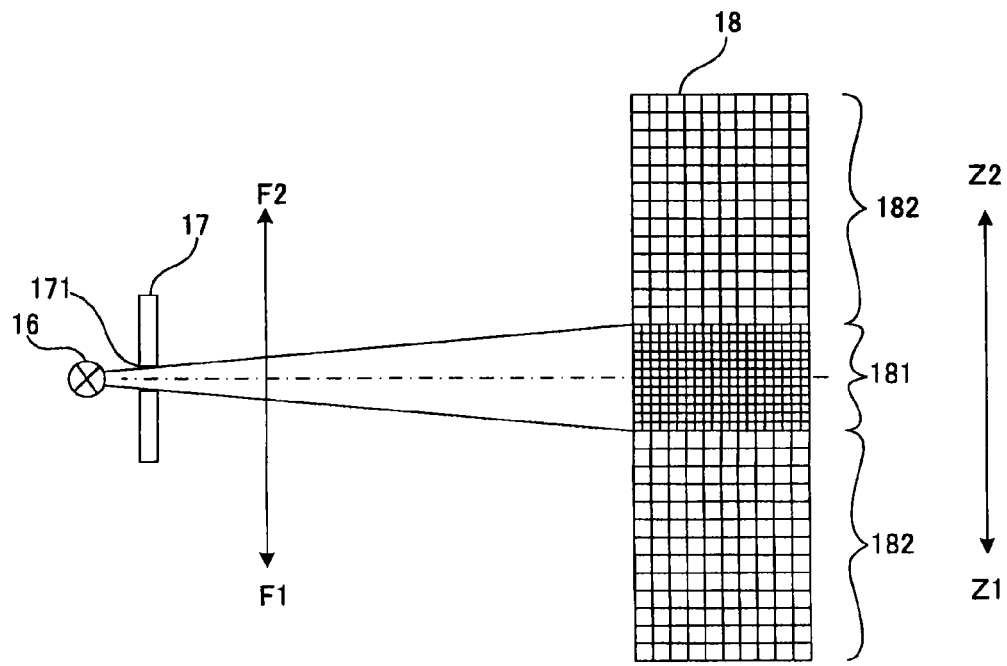
FIG. 7 is a drawing illustrating an X-ray detector of a hybrid type according to another comparative example.

Subsequently, the X-ray detector 18 illustrated in FIG. 3 is described with reference to another comparative example. FIG. 7 is a drawing illustrating the X-ray detector 18 of a hybrid type according to the comparative example. As illustrated in FIG. 7, the small detection range 181 is arrayed in the center of the X-ray detector 18 in the rostrocaudal direction, with the large detection range 182 arrayed in front and back of the small detection range 181.

According to the X-ray detector 18 of the comparative example, in which the small detection range 181 is arrayed in the center of the X-ray detector 18 in the rostrocaudal direction (Z direction), the focal point F3 of the middle focal point size corresponds to the small detection range 181, and the focal point F1 of the small focal point size does not always correspond to the small detection range 181. As a result, the X-ray detection elements of the small detector size cannot be fully utilized.

On the contrary, according to the X-ray detector 18 illustrated in FIG. 3, the small detection range 181 is allowed to correspond to the focal point F1 of the small focal point size by providing the small detection range 181 on one end of the X-ray detector 18, making it possible to fully utilize the X-ray detection elements of the small detector size.

[Second Embodiment]

In the above first embodiment, the X-ray detector 18 provided with the small detection range 181 at one end in the rostrocaudal direction (Z direction) is described, while the focal point F1 of small focal point size is allowed corresponding to the small detection range 181. Thereby, it becomes possible to achieve high resolution upon imaging. In addition, as the comparative example, the X-ray detector 18 of a hybrid type in which the small detection range 181 is provided in the center in the rostrocaudal direction is described, while the focal point F3 of the middle focal point size is allowed corresponding to the small detection range 181. Thereby, high resolution cannot be obtained upon imaging.

The X-ray detector 18 of a hybrid type according to the comparative example illustrated in FIG. 7 is fixed to the rotating frame 12 so as not to transfer. However, in even such the X-ray detector 18 of a hybrid type, in order to achieve high resolution upon imaging, the X-ray detector 18 is configured so as to be capable of transferring in the rostrocaudal direction (Z direction) such that the small detection range 181 corresponds to the focal point F1 of the small focal point size.

Next, an X-ray CT apparatus according to a second embodiment is described with reference to FIG. 8 and FIG. 9. In the second embodiment, configurations different from the first embodiment are mainly described, with descriptions of the same configurations as the first embodiment herein omitted.

An example of a unit for transferring the X-ray detector 18 in the rostrocaudal direction is described. A transfer unit includes a first rail, a second rail, a rack, a pinion, and a motor. The first rail is fixed to the rotating frame 12. The second frame is fitted in the first frame such that it is capable of being guided in the rostrocaudal direction. The X-ray detector 18 is provided in the second frame. The rack is fixed to either the rotating frame 12 or the X-ray detector 18 to be elongated in the rostrocaudal direction. The motor is mounted on the other of the rotating frame 12 or the X-ray detector 18. The pinion is engaged with the rack and rotated by the motor.

The pinion is relatively transferred in the rostrocaudal direction while being engaged with the rack due to rotation of the motor in the transfer unit. Thereby, the second frame is transferred in the rostrocaudal direction under the guidance of the first frame. This causes the X-ray detector 18 to transfer in the rostrocaudal direction. Relative transfer of the first rail and second rail is prevented by stopping rotation of the motor because the pinion is engaged with the rack. Thereby, the X-ray detector 18 is held in a specific position (for example, a first position or a second position to be described later.)

Figure 8:
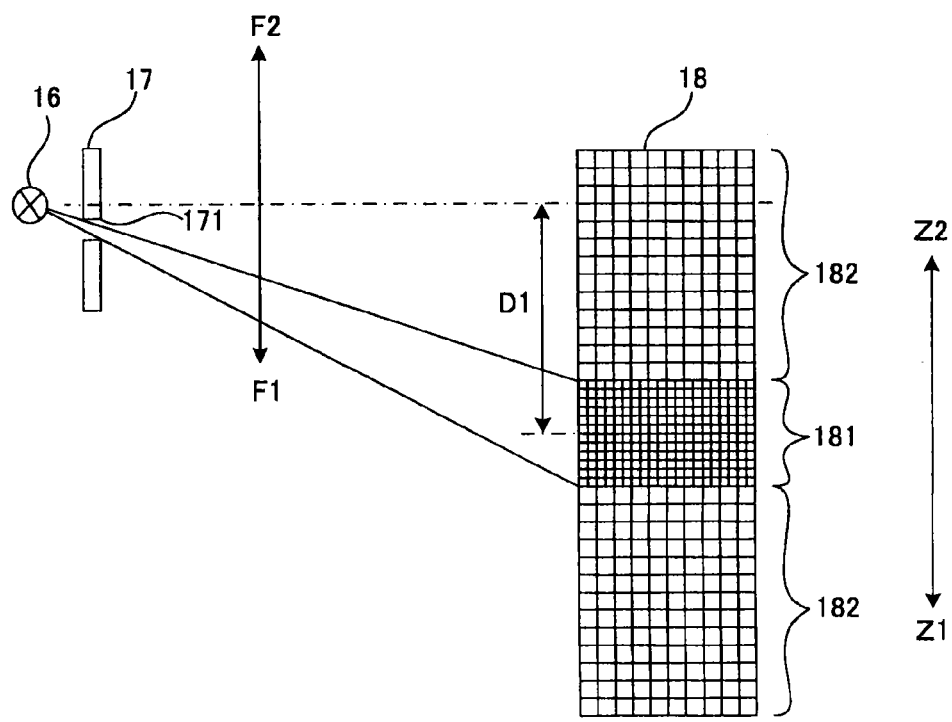
FIG. 8 is a drawing illustrating an X-ray detector transferred so as to allow a small detection range to correspond to a focal point of a small focal point size according to a second embodiment.

FIG. 8 is a drawing illustrating the X-ray detector transferred so as to allow a small detection range to correspond to the focal point of a small focal point size.

As illustrated in FIG. 8, the X-ray detector 18 includes the small detection range 181 arranged in the center of the rostrocaudal direction (Z direction). In addition, the large detection range 182 is arranged in front and back of the small detection range 181.

The X-ray detector 18 is configured so as to be capable of being transferred in the rostrocaudal direction (Z direction). A first position D1 of the X-ray detector 18 has been determined in advance in response to the first mode for achieving high resolution upon imaging. A second position D2 of the X-ray detector 18 has been determined in advance in response to the second mode for achieving low resolution upon imaging.
(Operation: First Mode)

The system controller 40 receives input regarding the first mode, and outputs the first position D1 to the scan controller 41. The scan controller 41 transfers the X-ray detector 18 based on the first position D1.

In addition, the system controller 40 receives input regarding the first mode, and outputs the range and position of the aperture 171 of the collimator 17 to the scan controller 41. The scan controller 41 transfers the collimator 17 based on the range and position of the aperture 171.

The focal point F1 of the small focal point size is allowed to correspond to the small detection range 181 by controlling the X-ray detector 18 and the collimator 17 by means of the scan controller 41. The small detection range 181 detects the X-rays radiated from the focal point F1 of the small focal point size and transmitted through the subject. This makes it possible to achieve high resolution upon imaging.
(Operation: Second Mode)

Figure 9:
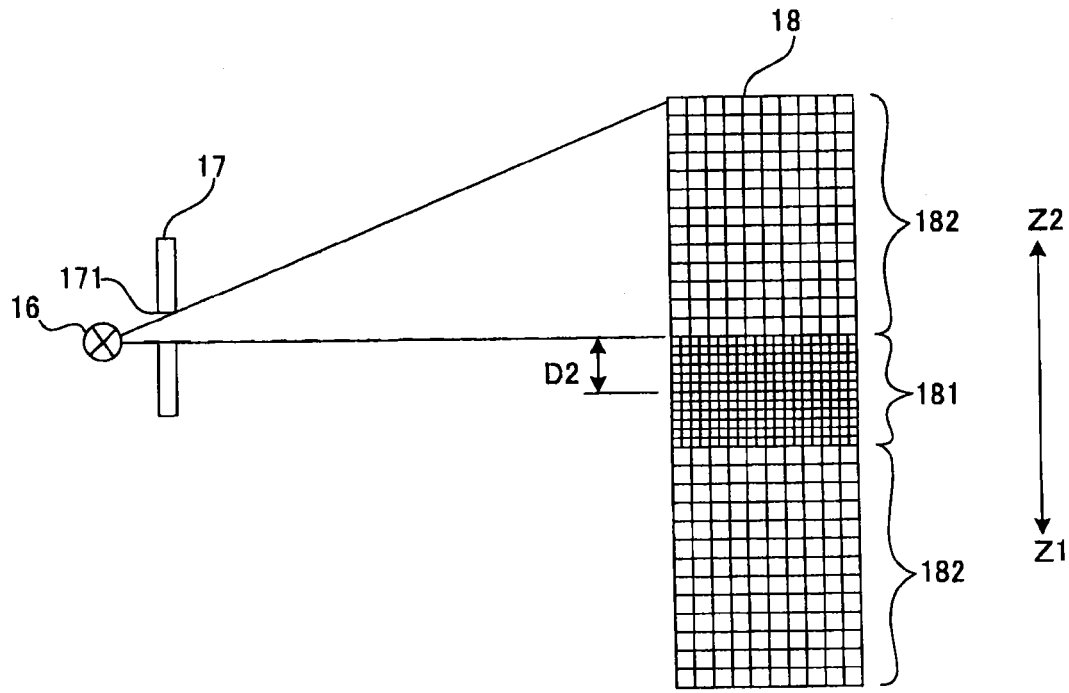
FIG. 9 is a drawing illustrating the X-ray detector transferred so as to allow a large detection range to correspond to a focal point of a large focal point size.

FIG. 9 is a drawing illustrating the X-ray detector transferred so as to allow a large detection range to correspond to the focal point of a large focal point size.

The system controller 40 receives input regarding the second mode, and outputs the second position D2 to the scan controller 41. The scan controller 41 transfers the X-ray detector 18 based on the second position D2.

In addition, the system controller 40 receives input regarding the second mode, and outputs the range and position of the aperture 171 of the collimator 17 to the scan controller 41. The scan controller 41 transfers the collimator 17 based on the range and position of the aperture 171.

The focal point F2 of the large focal point size is allowed to correspond to the large detection range 182 by controlling the X-ray detector 18 and the collimator 17 by means of the scan controller 41. The large detection range 182 detects the X-rays radiated from the focal point F2 of the large focal point size and transmitted through the subject. This makes it possible to achieve low resolution upon imaging.
[Third Embodiment]

The uniform type of X-ray detector 18 illustrated in FIG. 6 is entirely configured by the large detection range 182 so that the detector size of the X-ray detection elements corresponding to the focal point F1 of the small focal point size becomes large. Therefore, high resolution cannot be achieved upon imaging. On the contrary, it becomes possible to make the detector size smaller by tilting the X-ray detector 18 with respect to the X-ray tube 16.

Further, a third embodiment is described assuming that the X-ray CT apparatus 1 includes the uniform type of X-ray detector 18; however, it is obvious that the hybrid type of X-ray detector 18 may be used instead. In other words, it becomes possible to make the detector size of the small detection range 181 smaller by tilting the small detection range 181 with respect to the X-ray tube 16.

Next, the X-ray CT apparatus according to the third embodiment is described with reference to FIG. 10 to FIG. 12. In the third embodiment, configurations different from the first embodiment are mainly described, with descriptions of the same configurations as the first embodiment herein omitted.

An example of a unit for tilting the X-ray detector 16 is simply described. A tilting unit includes a base, an output gear, a pinion, and a motor. The base is fixed to the X-ray detector 18. The output gear is fixed to the base and includes a rotational axis around a tilt center. The motor is fixed to the rotating frame 12. The pinion is engaged with the output gear and rotated by the motor.

The pinion rotates the output gear around the tilt center due to rotation of the motor in the tilting unit. In this way, the base and the X-ray detector 16 are tilted towards the tilt center. Tilting of the base is prevented by stopping the rotation of the motor as the pinion is engaged with the output gear. Thereby, the X-ray detector 16 is held in a specific position (for example, a horizontal position D3, a tilted position D4 to be described later.)

The uniform type entirely configured by the large detection range 182 is used for the X-ray detector 18.

Figure 10:
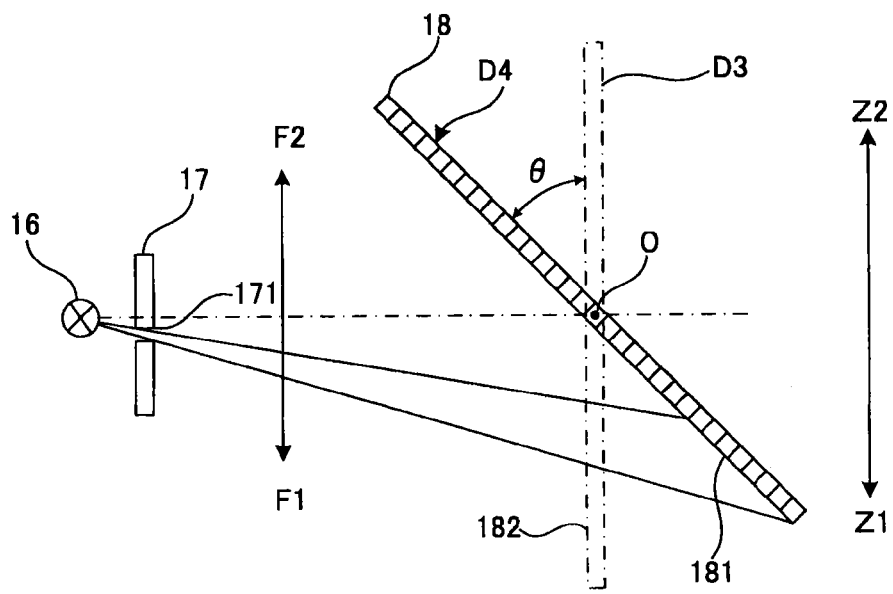
FIG. 10 is a drawing illustrating an X-ray detector tilted to an X-ray tube according to a third embodiment.

FIG. 10 is a drawing illustrating the X-ray detector 18 tilted with respect to the X-ray tube. The angle at which the X-ray detector 18 is tilted is denoted by "θ" in FIG. 10. The detector size is decreased by tilting the X-ray detector 18 with respect to the X-ray tube 16.

Next, the change in the detector size is described with reference to FIG. 11. FIG. 11 is a drawing illustrating changing of focal point sizes.

Figure 11:
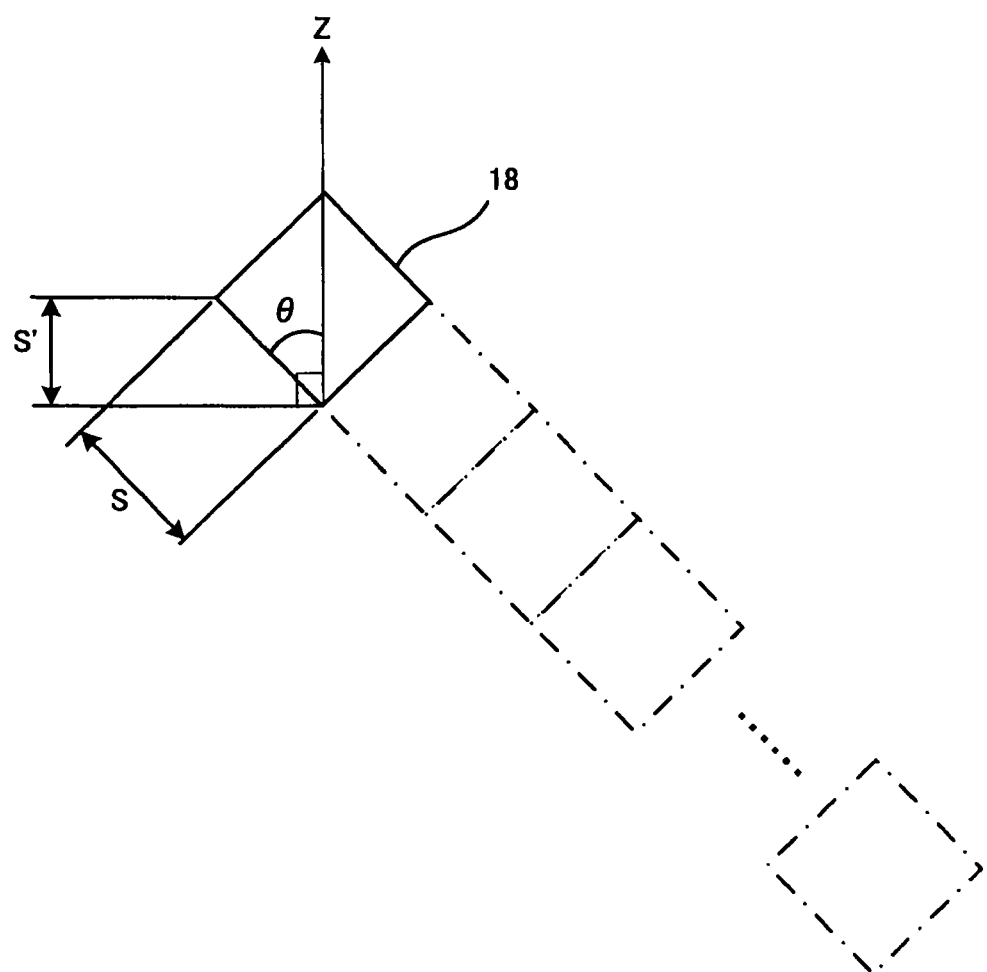
FIG. 11 is a drawing illustrating changing of focal point sizes.

As illustrated in FIG. 11, assuming that the detection size before the X-ray detector 18 is tilted is "S" and the detector size when the X-ray detector 18 is tilted by "θ" in the Z direction is "S'," "S'" is represented by the following formula.

$$S'=S*\cos\theta \qquad (1)$$

wherein, the sizes of the members partitioning the adjacent X-ray detection elements from each other are ignored.

Figure 12:
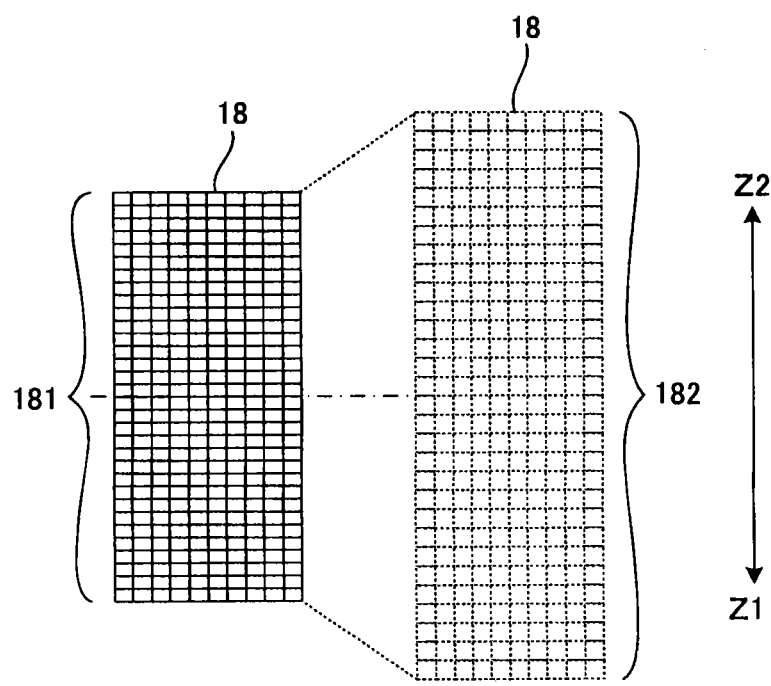
FIG. 12 is a drawing illustrating the tilted X-ray detector and the X-ray detector before the detector is tilted.

FIG. 12 is a drawing illustrating the tilted X-ray detector 18 on the left side and the X-ray detector 18 before the detector 18 is tilted on the right side.

By tilting the X-ray detector 18, the detector size thereof is decreased. This means that the X-ray detector 18 entirely configured by the large detection range 182 in the position before being tilted (the horizontal position denoted by D3 in FIG. 10) is replaced with the X-ray detector 18 entirely configured by the small detection range 181 in the position after being tilted (the tilted position denoted by D4 in FIG. 10.)

Accordingly, high resolution can be achieved upon imaging by allowing the small detection range 181 to correspond to the focal point F1 of the small focal point size. In addition, the small detection range 181 can be created by tilting the X-ray detector 18 even if the X-ray detector 18 is not configured by the small detection range 181.
(Operation: Second Mode)

The system controller 40 receives input regarding the second mode, and outputs the horizontal position D3 to the scan controller 41. The scan controller 41 horizontally tilts the X-ray detector 18 based on the horizontal position D3.

In addition, the system controller 40 receives input regarding the second mode, and outputs the range and position of the aperture 171 of the collimator 17 to the scan controller 41. The scan controller 41 transfers the collimator 17 based on the range and position of the aperture 171.

The focal point F2 of the large focal point size corresponds to the large detection range 182 (the large detection range illustrated on the right side of FIG. 12) by controlling the X-ray detector 18 and the collimator 17 by means of the scan controller 41. The large detection range 182 detects the X-rays radiated from the focal point F2 of the large focal point size and transmitted through the subject. This makes it possible to achieve low resolution upon imaging.

(Operation: First Mode)

The system controller 40 receives input regarding the first mode, and outputs the tilted position D4 to the scan controller 41. The scan controller 41 tilts the X-ray detector 18 based on the tilted position D4.

In addition, the system controller 40 receives input regarding the first mode, and outputs the range and position of the aperture 171 of the collimator 17 to the scan controller 41. The scan controller 41 transfers the collimator 17 based on the range and position of the aperture 171.

The focal point F1 of the small focal point size corresponds to the small detection range 181 (the small detection range illustrated on the left side of FIG. 12) by controlling the X-ray detector 18 and the collimator 17 by means of the scan controller 41. The small detection range 181 detects the X-rays radiated from the focal point F1 of the small focal point size and transmitted through the subject. This makes it possible to achieve high resolution upon imaging.

The first mode for limiting imaging to high resolution imaging and the second mode for limiting imaging to low resolution imaging are described as scan modes in the above description of the embodiment; however, a third mode for removing these limitations is also available. The projection data imaged at high resolution and the projection data imaged at low resolution can be acquired in the third mode, making it possible to reconstruct desired images using those projection data.

Figure 13:
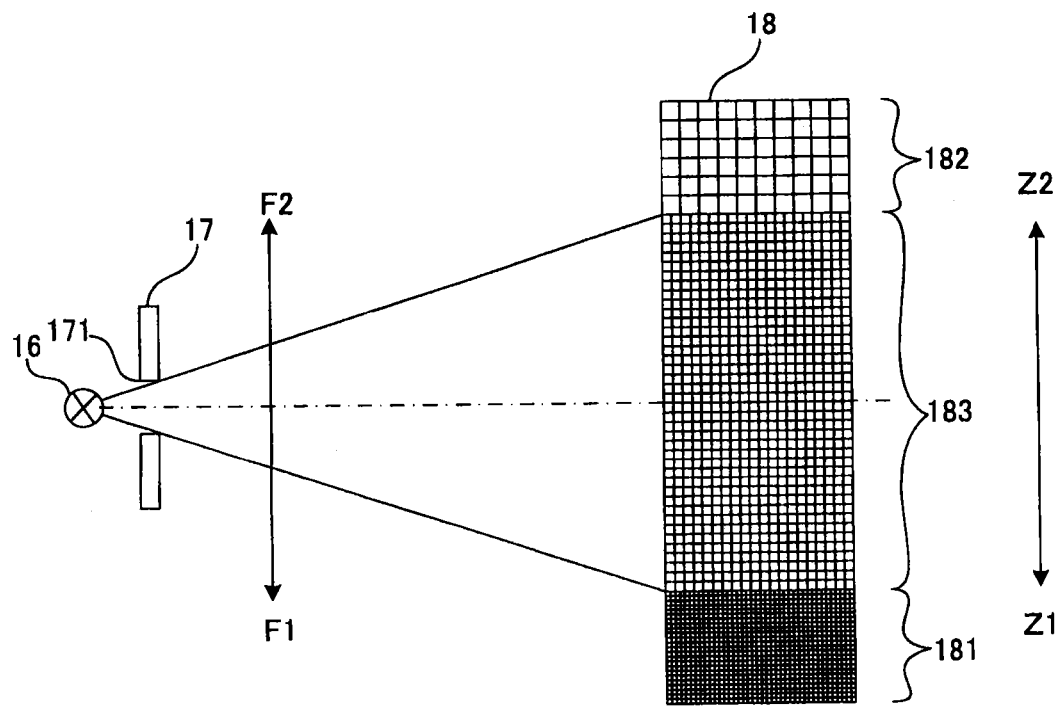
FIG. 13 is a drawing illustrating the X-ray detector provided with a middle detection range.

FIG. 13 is a drawing illustrating the X-ray detector 18 provided with a middle detection range 183. In the above-described embodiment, by controlling the collimator 17 and the X-ray detector 18 by means of the scan controller 41, the focal point F1 of the small focal point size is allowed to correspond to the small detection range 181, while the focal point F2 of the large focal point size is allowed to correspond to the large detection range 182. In addition, as illustrated in FIG. 13, the scan controller 41 may control the collimator 17, and the like to allow the focal point of a focal point size midway between the focal point F1 and the focal point F2 to correspond to the middle detection range 183, which is provided with a size midway between the small detection range 181 and the large detection range 182.

Figure 14:
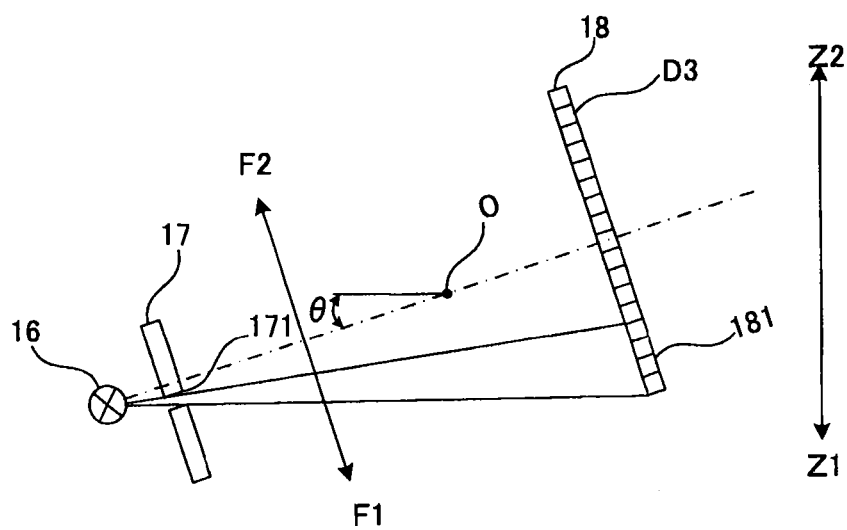
FIG. 14 is a drawing illustrating a tilted gantry.

FIG. 14 is a drawing illustrating the tilted gantry 10. In the embodiment, the X-ray detector 18 alone is tilted; however, as illustrated in FIG. 14, the X-ray tube 16, the collimator 17, and the X-ray detector 18 may be tilted as a whole in the rostrocaudal direction by tilting the gantry 10. This makes it possible to allow the focal point F1 of the small focal point size to correspond to the small detection range 181.

Figure 15:
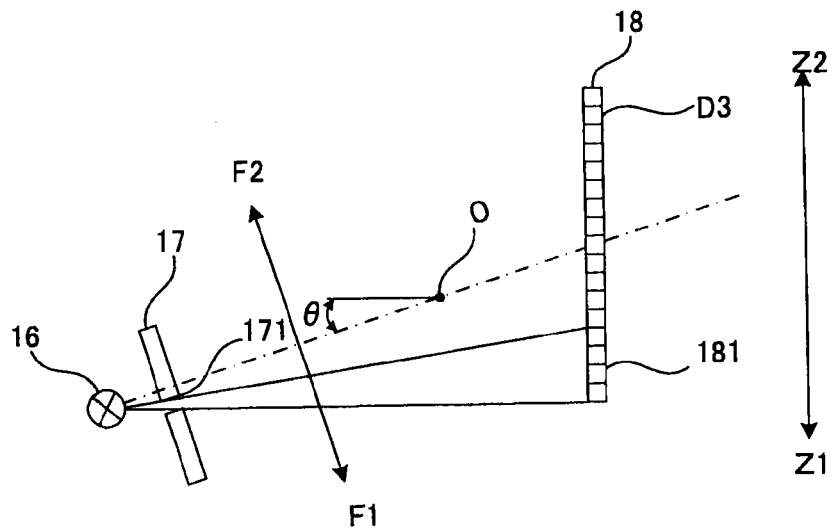
FIG. 15 is a drawing illustrating the X-ray detector rotated in parallel with the body axis from the posture illustrated in FIG. 14.

Further, as illustrated in FIG. 15, the X-ray detector 18 may be rotated to the posture parallel to the body axis (Z-axis) from the posture tilted to the body axis illustrated in FIG. 14. In addition, in this case, it becomes possible to allow the focal point F1 of the small focal point size to correspond to the small detection range 181.

[Fourth Embodiment]

Next, an X-ray CT apparatus according to a fourth embodiment is described with reference to FIG. 16 and FIG. 17.

In the fourth embodiment, configurations different from the first embodiment are mainly described, with descriptions of the same configurations as the first embodiment herein omitted.

In the configurations of the above-described embodiment, a small detection range 181 is allowed corresponding to the focal point F1 of the small focal point size by controlling the collimator 17, and the detector size is decreased by tilting the X-ray detector 18 towards the X-ray tube 16. Thereby, high resolution can be achieved upon imaging. In other words, in order to achieve high resolution, any configuration serves to control the collimator 17 and the X-ray detector 18 other than the X-ray tube 16.

On the contrary, in the fourth embodiment, a control unit is configured such that the focal point size is changed to the size of the focal point F1 by tilting the radiation surface 162 of the X-ray tube 16. The method of tilting the radiation surface 162 may include tilting the anode 161 towards the filament 164 (refer to FIG. 2) or tilting the anode 161 together with the filament 164. As described above, the control unit corresponds to the system controller 40 and the scan controller 41.

Figure 16:
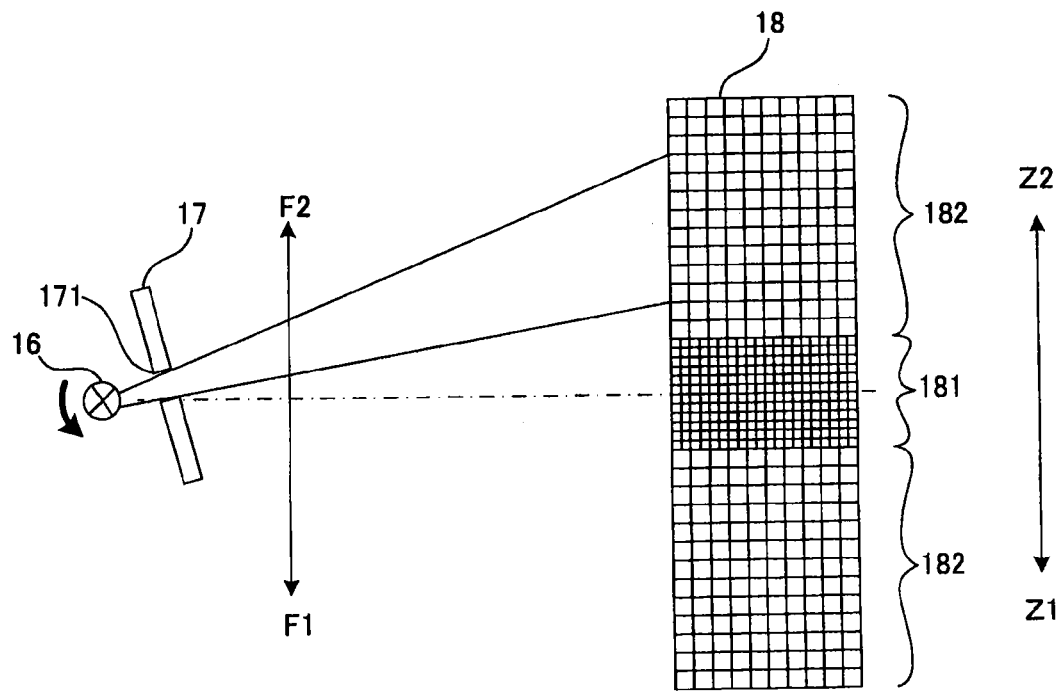
FIG. 16 is a drawing illustrating a radiation surface of an X-ray tube tilted anticlockwise according to a fourth embodiment.

FIG. 16 is a drawing illustrating the radiation surface 162 of the X-ray tube 16 tilted anticlockwise. As illustrated in FIG. 16, the focal point F2 of the large focal point size is achieved by tilting the radiation surface 162 anticlockwise. Then, the X-rays from the focal point F2 are detected by the large detection range 182. The focal point F2 is allowed to correspond to the large detection range 182. Thereby, noise from the projection data obtained through CT scanning is reduced, making it possible to clarify concentration differences between images.

The focal point F1 of the small focal point size may be allowed to correspond to the small detection range 181 in order to achieve high resolution of image from the condition of FIG. 16, which illustrates clear concentration differences between images.

Figure 17:
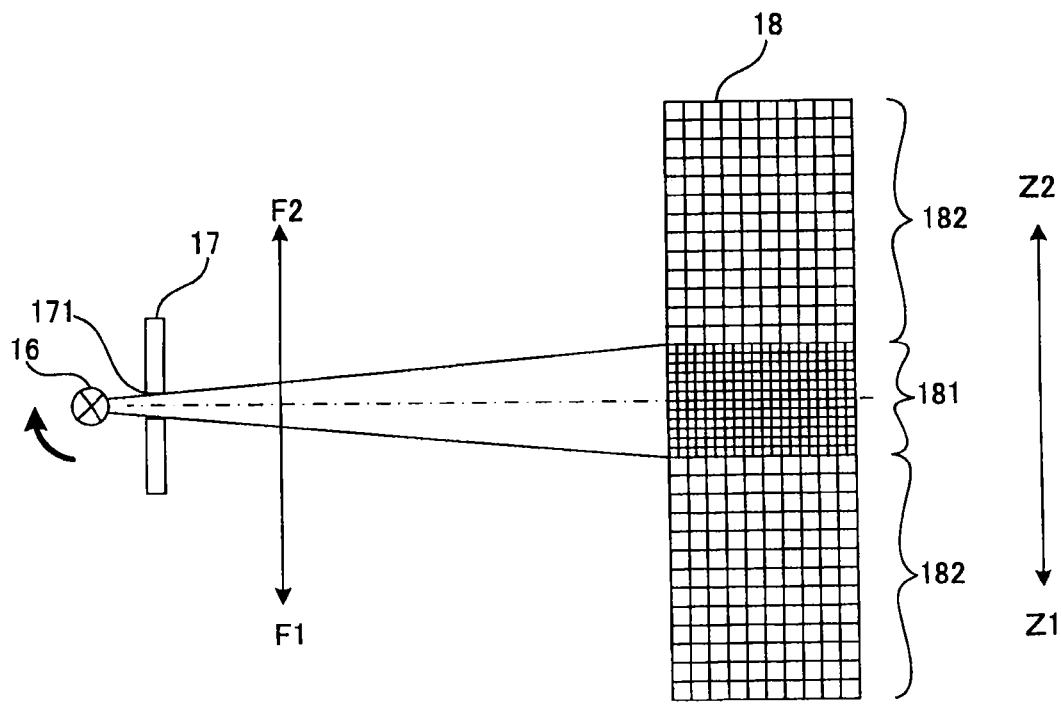
FIG. 17 is a drawing illustrating the radiation surface of the X-ray tube tilted clockwise.

FIG. 17 is a drawing illustrating the radiation surface 162 of the X-ray tube 16 tilted clockwise. As illustrated in FIG. 17, the focal point F1 of the small focal point size is achieved by tilting the radiation surface 162 clockwise. Then, the X-rays from the focal point F1 are detected by the small detection range 181. Thereby, high image resolution can be achieved based on the projection data acquired through CT scanning.

The configuration is indicated, in which the X-rays from the radiation surface 162 are detected within the small detection range 181 and the large detection range 182 by tilting the radiation surface 162 using the hybrid type of X-ray detector 18 with the small detection range 181, the large detection range 182, and the like. arranged; however, other configurations are also available. Desired images may be acquired by changing the focal point size into the size of the focal point F1 or the size of the focal point F2 by tilting the radiation surface 162 using, for example, the uniform type of X-ray detector 18 with the middle detection range 183 uniformly arranged, as the X-ray detector 18.

[Fifth Embodiment]

Next, an X-ray CT apparatus according to a fifth embodiment is described with reference to FIG. 18 to FIG. 20.

In the fifth embodiment, configurations different from the first embodiment are mainly described, with descriptions of the same configurations as the first embodiment herein omitted.

In the fourth embodiment, in order to achieve high resolution, the control unit is configured such that the focal point size is changed to the size of the focal point F1 by tilting the radiation surface 162 of the X-ray tube 16.

On the contrary, in the fifth embodiment, a control unit is configured such that the small detection range 181 or the large detection range 182 is selected by transferring the radiation surface 162. The method of transferring the radiation surface 162 includes transferring the anode 161 to the filament 164 (refer to FIG. 2) or transferring the anode 161 together with the filament 164. Here, the direction to transfer the anode 161, or the like, is the longitudinal direction (Z-axis (body axis) direction.)

Figure 18:
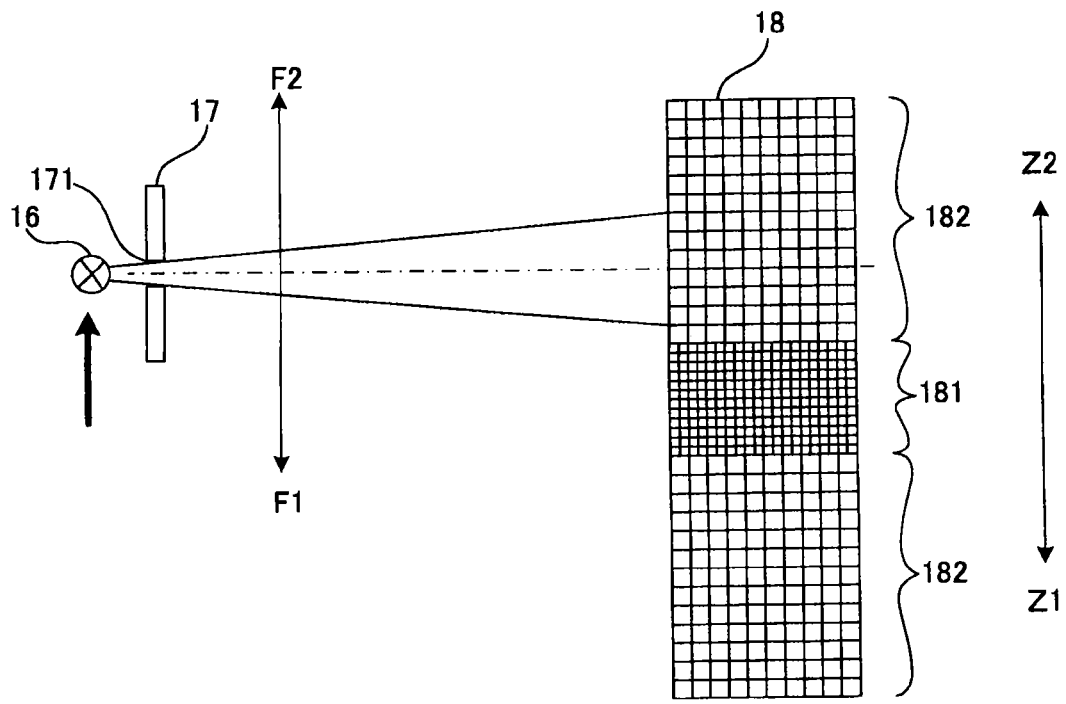
FIG. 18 is a drawing illustrating a radiation surface of an X-ray tube transferred in the Z2 direction according to a fifth embodiment.

FIG. 18 is a drawing illustrating the radiation surface of the X-ray tube transferred in the Z2 direction. As illustrated in FIG. 18, the X-rays from the radiation surface 162 of the X-ray tube 16 are detected by the large detection range 182 by transferring the radiation surface 162 in the Z2 direction. Thereby, noise of the projection data obtained through CT scanning is reduced, making it possible to clarify concentration differences between images.

The X-rays from the images radiation surface 16 may be detected from the small detection range 181 in order to achieve high image resolution from the condition of FIG. 18, which illustrates clear concentration differences between images.

Figure 19:
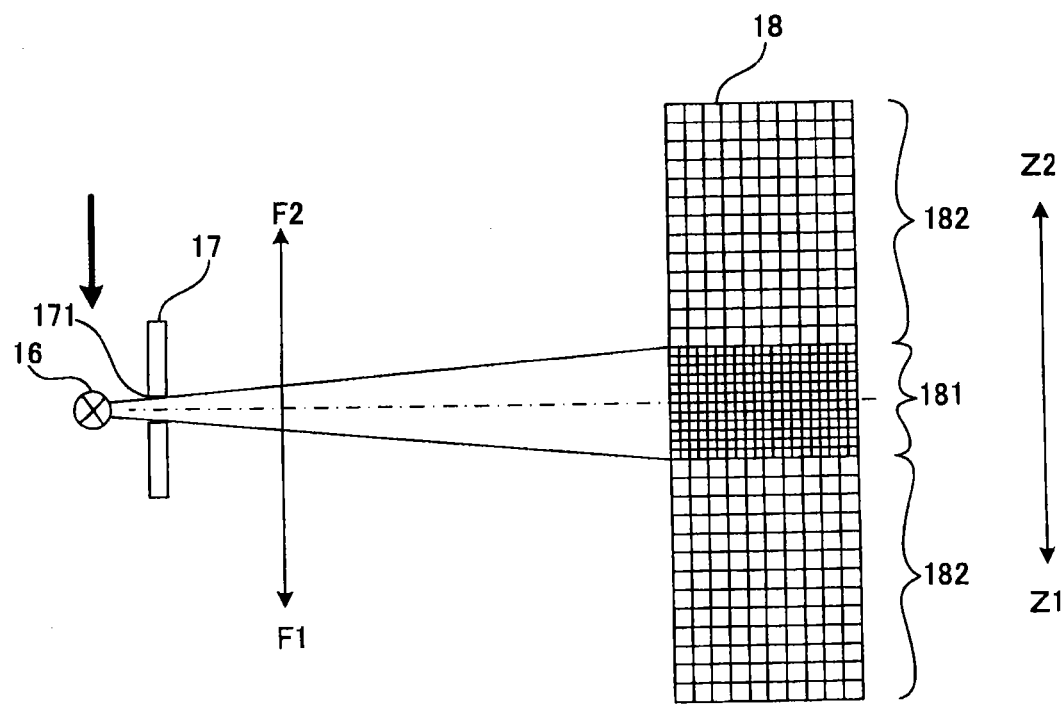
FIG. 19 is a drawing illustrating the radiation surface of the X-ray tube transferred in a Z1 direction.

FIG. 19 is a drawing illustrating the radiation surface 162 transferred in the Z1 direction. The X-rays from the radiation surface 162 are detected by the small detection range 181 by transferring the radiation surface 162 in the Z1 direction as illustrated in FIG. 19. Thereby, high image resolution can be achieved based on the projection data acquired through CT scanning.

Further, FIG. 18 and FIG. 19 illustrate the configurations in which the radiation surface 162 is transferred in order to acquire the desired images; however, it is obvious that, in addition to this, the radiation surface 162 may be relatively transferred to the X-ray detector 18.

Figure 20:
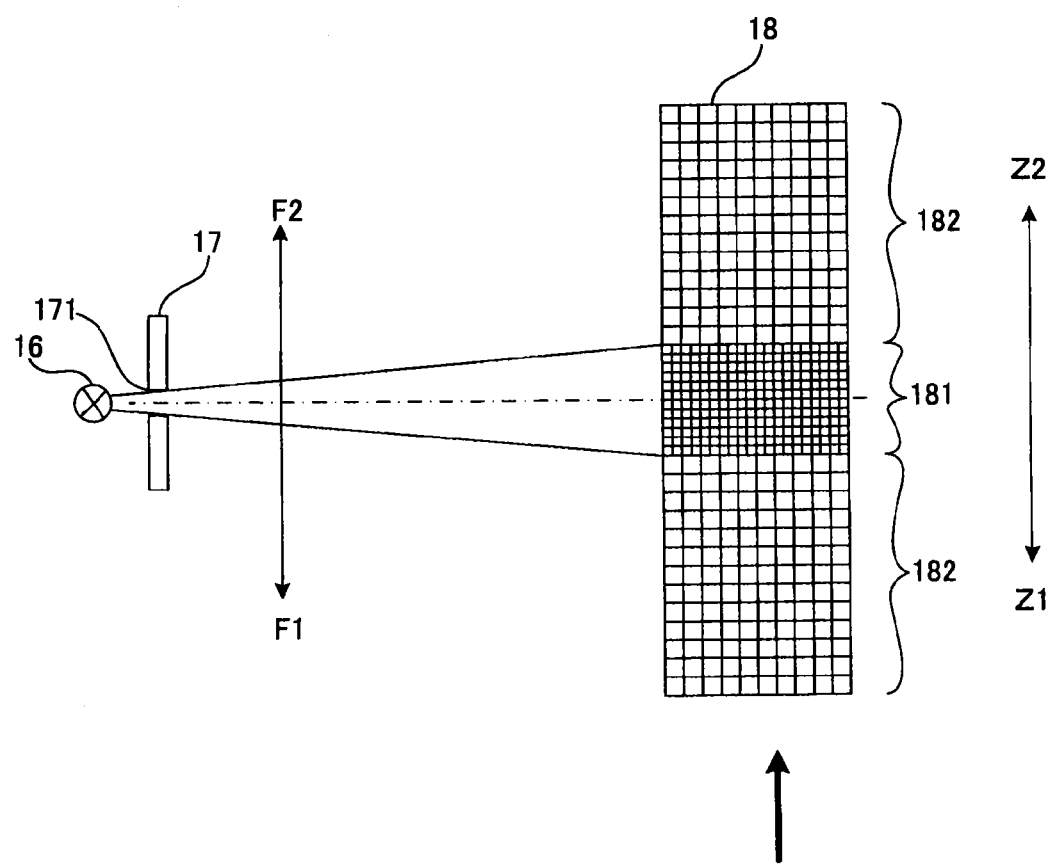
FIG. 20 is a drawing illustrating the radiation surface of the X-ray tube transferred relative to the X-ray detector.

FIG. 20 is a drawing illustrating the radiation surface relatively transferred to the X-ray detector. For example, the X-rays from the radiation surface 162 are detected by the small detection range 181 by transferring the X-ray detector 18 in the Z2 direction in order to achieve high image resolution from the condition of FIG. 18, which illustrates clear concentration differences between images. Thereby, high image resolution can be achieved based on the projection data acquired through CT scanning. The X-rays from the radiation surface 162 are detected by the small detection range 181 by transferring the X-ray detector 18 in the Z1 direction in order to acquire images with clear concentration differences.

The present invention can be specified by modifying the constituent elements without departing form the scope of the invention in its implementation phase, without being limited to the above-described embodiments as they are. In addition, various inventions can be created according to appropriate combinations of a plurality of constituent elements disclosed in the above-described embodiments. For example, some constituent elements may be deleted from all the constituent elements described in the embodiments. Further, the constituent elements in the different embodiments may be appropriately combined.

EXPLANATION OF THE SYMBOLS

1 X-ray CT apparatus
10 gantry
12 rotating frame
14 table top
16 X-ray tube
161 anode
162 radiation surface (target)
163 cathode
164 filament
17 collimator
18 X-ray detector
181 small detection range
182 large detection range
183 middle detection range
20 rotary driving unit
22 high voltage generator
24 top transfer unit
26 data acquisition system (DAS)
30 console
31 preprocessor
32 reconstructor
40 system controller
41 scan controller
44 operation unit
45 display
46 storage

The invention claimed is:

1. An X-ray CT apparatus configured to rotate an X-ray tube and an X-ray detector around a subject mounted on a table top, radiate X-rays with a cone angle enlarging from the X-ray tube to the subject, and acquire images of the subject based on the X-rays transmitted through the subject and detected by the X-ray detector, the X-ray CT apparatus comprising:
the X-ray tube, which includes a radiation surface of the X-rays and is configured such that a size of an effective focal point, which is a point when the radiation surface is viewed from a side on which the X-rays are radiated, is small at one end of the cone angle and is increased toward another end of the cone angle;
the X-ray detector, which is configured to include at least two divided ranges,
one range is configured to include a small detection range in which X-ray detection elements of a small size for detecting the X-rays radiated from the X-ray tube are arrayed,
the other range is configured to include a large detection range in which X-ray detection elements of a large size for detecting the X-rays radiated from the X-ray tube are arrayed, and
the radiation surface and the X-ray detector are configured such that positions thereof are transferable; and
a control unit configured to select the small detection range or the large detection range, and transfer the positions according to the detection range selected and a position of the detection range to detect X-rays from the effective focal point in a size corresponding to the size of the X-ray detection elements of the X-ray detector.

2. The X-ray CT apparatus according to claim 1, wherein the small detection range and the large detection range are arrayed in a longitudinal direction of the X-ray detector,
when the small detection range is selected, the control unit transfers a position of the X-ray detector in the longitudinal direction such that the small detection range is located in a position for detecting the X-rays from the effective focal point in a small size at the one end of the cone angle, and
when the large detection range is selected, the control unit transfers a position of the X-ray detector in the longitudinal direction such that the large detection range is located in a position for detecting the X-rays from the effective focal point in a large size at the other end of the cone angle.

3. The X-ray CT apparatus according to claim 2, wherein the control unit is configured to tilt the radiation surface when changing the size of the effective focal point.

4. The X-ray CT apparatus according to claim 3, further comprising:
a collimator with an aperture through which the X-rays are transmitted configured to limit a path of the X-rays to the subject by adjusting range and position of the aperture, wherein
the control unit is configured to allow the effective focal point of the small size to correspond to the small detection range by controlling the X-ray detector and the collimator.

5. The X-ray CT apparatus according to claim 1, wherein the control unit is configured to transfer the radiation surface relative to the X-ray detector when selecting the small detection range or the large detection range.

6. The X-ray CT apparatus according to claim 5, further comprising:
a collimator with an aperture through which the X-rays are transmitted configured to limit a path of the X-rays to the subject by adjusting range and position of the aperture, wherein
the control unit is configured to allow the effective focal point of the small size to correspond to the small detection range by controlling the X-ray detector and the collimator.

7. The X-ray CT apparatus according to claim 1, wherein the small detection range is configured to be arrayed on one end in the longitudinal direction.

8. The X-ray CT apparatus according to claim 7, further comprising:
a collimator with an aperture through which the X-rays are transmitted configured to limit a path of the X-rays to the subject by adjusting range and position of the aperture, wherein
the control unit is configured to allow the effective focal point of the small size to correspond to the small detection range by controlling the X-ray detector and the collimator.

9. An X-ray CT apparatus configured to rotate an X-ray tube and an X-ray detector around a subject mounted on a table top, radiate X-rays with a cone angle enlarging from the X-ray tube to the subject, and acquire images of the subject based on the X-rays transmitted through the subject and detected by the X-ray detector, the X-ray CT apparatus comprising:
the X-ray tube, which is configured to include a radiation surface of the X-rays and be structured such that the size of an effective focal point that is a point when seeing the radiation surface from the side on which the X-rays are radiated is decreased at one end of the cone angle, while the size of the effective focal point is increased toward the other end of the cone angle;
the X-ray detector, which is configured to include at least two divided ranges,
one range is configured to include a small detection range in which X-ray detection elements of a small size for detecting the X-rays radiated from the X-ray tube are arrayed,
the other range is configured to include a large detection range in which the X-ray detection elements of a large size for detecting the X-rays radiated from the X-ray tube are arrayed, and
the radiation surface and the X-ray detector are configured such that positions thereof are transferable; and
a control unit configured to select the small detection range or the large detection range, and transfer the positions according to the detection range selected and a position of the detection range to detect X-rays from the effective focal point in a size corresponding to the size of the X-ray detection elements of the X-ray detector.

10. The X-ray CT apparatus according to claim 9, wherein:
the small detection range is configured to be arrayed in the center of the longitudinal direction; and
the X-ray detector is configured to be transferred, in the longitudinal direction, to a position where the X-rays radiated from the effective focal point of a small size on the at least one end are detected in the small detection range.

11. The X-ray CT apparatus according to claim 10, further comprising:
a collimator with an aperture through which the X-rays are transmitted configured to limit a path of the X-rays to the subject by adjusting range and position of the aperture, wherein
the control unit is configured to allow the effective focal point of the small size to correspond to the small detection range by controlling the X-ray detector and the collimator.

12. The X-ray CT apparatus according to claim 9, wherein the X-ray detector is configured to be tilted to the X-ray tube upon detection of the X-rays in the small detection range, thereby decreasing the size of the effective focal point when seeing from the small detection range.

13. The X-ray CT apparatus according to claim 12, further comprising:
a collimator with an aperture through which the X-rays are transmitted configured to limit a path of the X-rays to the subject by adjusting range and position of the aperture, wherein
the control unit is configured to allow the effective focal point of the small size to correspond to the small detection range by controlling the X-ray detector and the collimator.

14. The X-ray CT apparatus according to claim 9, further comprising:
a collimator with an aperture through which the X-rays are transmitted configured to limit a path of the X-rays to the subject by adjusting range and position of the aperture, wherein
the control unit is configured to allow the effective focal point of the small size to correspond to the small detection range by controlling the X-ray detector and the collimator.

15. The X-ray CT apparatus according to claim 9, wherein the control unit is configured to transfer the radiation surface relative to the X-ray detector when selecting the small detection range or the large detection range.

16. The X-ray CT apparatus according to claim 9, wherein the control unit is configured to tilt the radiation surface when changing the size of the effective focal point.

17. The X-ray CT apparatus according to claim 9, wherein the small detection range is configured to be arrayed on one end in the longitudinal direction.

* * * * *